(12) United States Patent
Han et al.

(10) Patent No.: US 11,298,481 B2
(45) Date of Patent: Apr. 12, 2022

(54) NON-GAS ANALYZER MONITOR OF INSPIRED GAS CONCENTRATION

(71) Applicant: 12th Man Technologies, Inc., Garden Grove, CA (US)

(72) Inventors: Steve Han, Huntington Beach, CA (US); Alex Stenzler, Long Beach, CA (US); Martin Stegenga, Seal Beach, CA (US)

(73) Assignee: 12th Man Technologies, Inc., Garden Grove, CA (US)

( * ) Notice: Subject to any disclaimer, the term of this patent is extended or adjusted under 35 U.S.C. 154(b) by 678 days.

(21) Appl. No.: 15/268,464

(22) Filed: Sep. 16, 2016

(65) Prior Publication Data

US 2017/0072152 A1 Mar. 16, 2017

Related U.S. Application Data

(60) Provisional application No. 62/219,211, filed on Sep. 16, 2015.

(51) Int. Cl.
*A61M 16/00* (2006.01)
*G01N 11/04* (2006.01)
(Continued)

(52) U.S. Cl.
CPC .... *A61M 16/0051* (2013.01); *A61M 16/0057* (2013.01); *A61M 16/125* (2014.02);
(Continued)

(58) Field of Classification Search
CPC .......... A61M 16/0051; A61M 16/0003; A61M 16/125; A61M 16/201; A61M 16/203; A61M 16/12; A61M 16/204; A61M 16/024; A61M 2016/0027; A61M 2016/003; A61M 2016/0033; A61M 2205/3334; G01N 33/0022; G01N 33/0031; G01N 33/0063;
(Continued)

(56) References Cited

U.S. PATENT DOCUMENTS 4,910,519 A 3/1990 Duell et al.
4,928,684 A 5/1990 Breitenfelder et al.
(Continued)

FOREIGN PATENT DOCUMENTS

WO 2013188458 A2 12/2013

*Primary Examiner* — Joseph D. Boecker
*Assistant Examiner* — Brian T Khong
(74) *Attorney, Agent, or Firm* — Riverside Law LLP

(57) ABSTRACT

A system for monitoring inspirable gas for delivery to a patient includes a branched breathing circuit having a first branch conduit and a second branch conduit. The first branch conduit is fluidly connected to a first gas source and the second branch conduit is fluidly connected to a second gas source, and the first and second branch conduits merge into a patient delivery conduit. The system includes a first flow sensor in the first branch conduit, a second flow sensor in the second branch conduit, and a third flow sensor in the patient delivery conduit. A control unit is electrically coupled to the first, second and third flow sensors. The control unit is configured to determine a blend of gas in the patient delivery circuit based on a measured flow from the third flow sensor and a measured flow from at least one of the first and second flow sensors.

27 Claims, 5 Drawing Sheets

(51) Int. Cl.
*A62B 7/02* (2006.01)
*A61M 16/20* (2006.01)
*A61M 16/12* (2006.01)
*G01N 33/00* (2006.01)

(52) U.S. Cl.
CPC ............. *A61M 16/204* (2014.02); *A62B 7/02* (2013.01); *G01N 11/04* (2013.01); *G01N 33/0022* (2013.01); *G01N 33/0031* (2013.01); *A61M 2205/3334* (2013.01)

(58) Field of Classification Search
CPC ........... G01N 33/0065; G01N 33/0067; G05D 11/132; G05D 16/2046
See application file for complete search history.

(56) References Cited

U.S. PATENT DOCUMENTS

| | | | |
|---|---|---|---|
| 5,069,220 A | 12/1991 | Casparie et al. | |
| 5,390,666 A | 2/1995 | Kimm et al. | |
| 5,433,193 A | 7/1995 | Sanders et al. | |
| 5,558,083 A | 9/1996 | Bathe et al. | |
| 5,806,513 A * | 9/1998 | Tham | A61M 16/104 128/203.12 |
| 6,089,229 A * | 7/2000 | Bathe | A61M 16/12 128/203.12 |
| 6,439,229 B1 * | 8/2002 | Du | A61M 16/026 128/204.21 |
| 8,459,258 B2 | 6/2013 | Slessarev et al. | |
| 2008/0078385 A1 * | 4/2008 | Xiao | A61M 16/1075 128/203.26 |
| 2009/0054798 A1 | 2/2009 | Varney et al. | |
| 2009/0120435 A1 * | 5/2009 | Slessarev | A61M 16/0051 128/203.14 |
| 2009/0183737 A1 | 7/2009 | Oberle et al. | |
| 2010/0071695 A1 * | 3/2010 | Thiessen | A61M 16/0816 128/204.18 |
| 2012/0272957 A1 * | 11/2012 | Chapman | A61M 16/0045 128/203.12 |
| 2012/0312302 A1 * | 12/2012 | Cardelius | A61M 16/104 128/203.14 |
| 2013/0239968 A1 | 9/2013 | Friberg et al. | |
| 2013/0340753 A1 * | 12/2013 | Weiszl | A61M 16/12 128/203.14 |
| 2014/0150795 A1 * | 6/2014 | Milne | A61M 16/0051 128/205.23 |
| 2015/0320953 A1 * | 11/2015 | Acker | A61M 16/12 128/203.14 |
| 2015/0374947 A1 * | 12/2015 | Wallen | A61M 16/01 128/202.22 |
| 2016/0287824 A1 * | 10/2016 | Chang | A61M 16/0066 |
| 2017/0246419 A1 * | 8/2017 | Callaghan | A61M 16/12 |

* cited by examiner

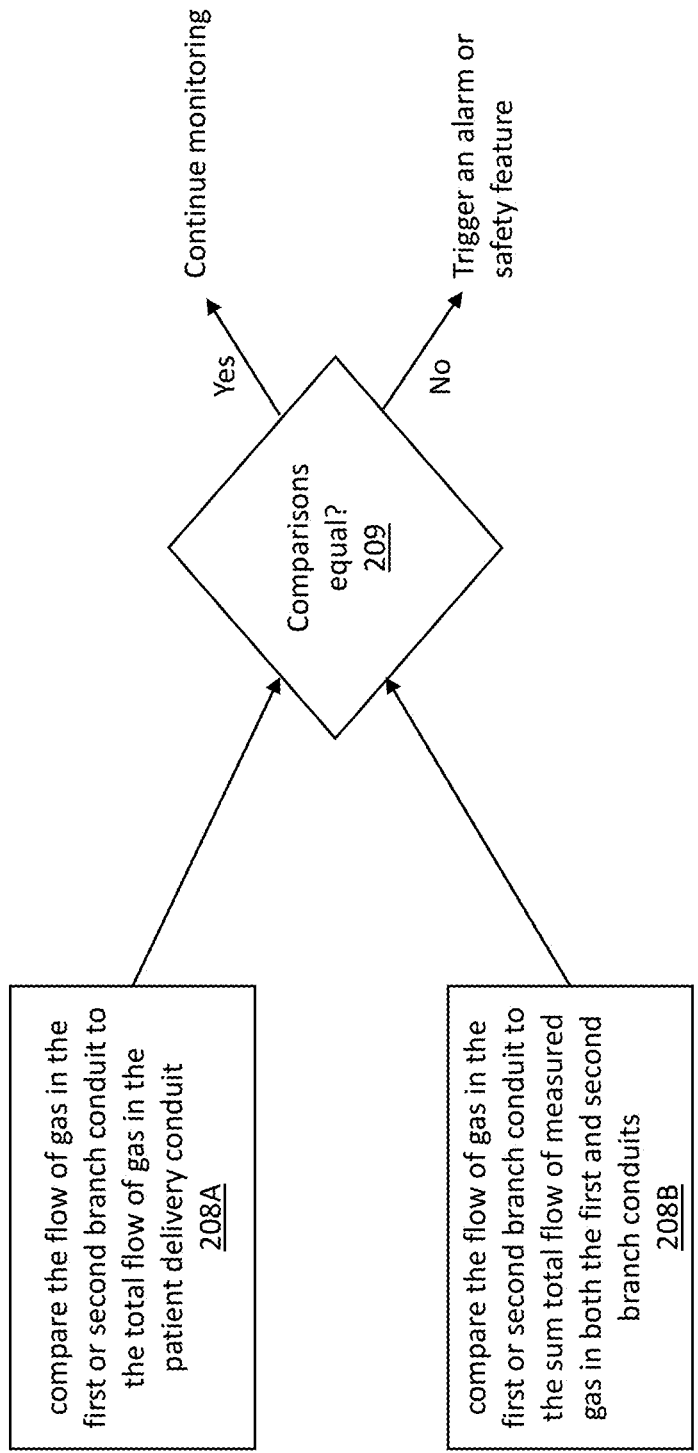

NON-GAS ANALYZER MONITOR OF INSPIRED GAS CONCENTRATION

CROSS-REFERENCE TO RELATED APPLICATIONS

This application claims priority to U.S. provisional application No. 62/219,211 filed on Sep. 16, 2015 incorporated herein by reference in its entirety.

BACKGROUND OF THE INVENTION

Conventional methods of monitoring inspired gas concentrations typically utilize a gas analyzer and sensor system that is specific for the gas of interest. This usually requires an independent device or module containing the sensor, in many cases a sampling pump, and in most cases, calibration gases and procedures to assure accuracy. For example, in Bathe et al. (U.S. Pat. No. 5,558,083), a conventional gas analyzer or gas sensing bench is utilized to measure the gas concentrations of an airstream administered to the patient. The purpose of an independent monitor is to detect if and when an element of the gas mixing system malfunctions and delivers the wrong concentration of gas. However, these independent gas monitoring systems that use a gas specific sensor are complex and cumbersome, and can significantly increase the cost, time to operation, and technical requirements for usability of the system. They typically require the use of certified calibration gases and regulators for the cylinders which add to the complexity of the use of the monitoring devices while increasing the safety concerns for handling potentially high pressure calibration gas cylinders.

What is needed in the art is a system and method for monitoring inspired gas concentrations without the use of a complex or conventional gas analyzer.

SUMMARY OF THE INVENTION

In one embodiment, a system for monitoring an inspirable gas for delivery to a patient, including a branched breathing circuit comprising a first branch conduit and a second branch conduit, where the first branch conduit is fluidly connected to a first gas source and the second branch conduit is fluidly connected to a second gas source, and where the first and second branch conduits merge into a patient delivery conduit; a first flow sensor in the first branch conduit, a second flow sensor in the second branch conduit, and a third flow sensor in the patient delivery conduit; and a control unit electrically coupled to the first, second and third flow sensors, where the control unit is configured to determine a blend of gas in the patient delivery circuit based on a measured flow from the third flow sensor and a measured flow from at least one of the first and second flow sensors. In one embodiment, a system for monitoring an inspirable gas for delivery to a patient includes a branched breathing circuit including a first branch conduit and a second branch conduit, where the first branch conduit is fluidly connected to a first gas source and the second branch conduit is fluidly connected to a second gas source, and where the first and second branch conduits merge into a patient delivery conduit, a first flow sensor in the first branch conduit and a second flow sensor in the second branch conduit, a valve in the second branch conduit upstream of the second flow sensor, a third flow sensor in the patient delivery conduit, and a control unit electrically coupled to the valve and the first, second and third flow sensors, where the control unit is configured to adjust the valve to control the flow of gas from the second gas source according to a flow measurement signal received from each of the first, second and third flow sensors. In one embodiment, the second gas source is a pressurized container comprising the second gas. In one embodiment, the first gas source is at least one of a ventilator, room air and ambient air. In one embodiment, the first gas source is pressurized to a pressure differential of less than 3 psi. In one embodiment, the first gas source is unpressurized air. In one embodiment, the valve is a proportional flow control valve. In one embodiment, the control unit is a microcontroller. In one embodiment, the control unit is configured to send a correction signal to the valve based on a flow measurement signal received from the second flow sensor. In one embodiment, the control unit is configured to integrate flow measurement signals received from at least one of the first, second and third flow sensors and the correction signal. In one embodiment, the control unit is configured to integrate flow measurement signals received from all of the first, second and third flow sensors and the correction signal. In one embodiment, the control unit is configured to accept a source gas concentration value and a target patient gas concentration value as input. In one embodiment, the system includes a valve in the second branch conduit upstream of the second flow sensor, where the control unit is configured to adjust the valve based on the measured flow from the three flow sensors. In one embodiment, the control unit is configured to integrate a first flow measurement signal received from the first flow sensor and a second flow measurement signal received from the second flow sensor to calculate a concentration value of the second gas delivered through the patient delivery conduit. In one embodiment, the control unit is configured to integrate a first flow measurement signal received from the first flow sensor and a second flow measurement signal received from the third flow sensor to calculate a concentration value of the second gas delivered through the patient delivery conduit. In one embodiment, the control unit is configured to integrate a first flow measurement signal received from the second flow sensor and a second flow measurement signal received from the third flow sensor to calculate a concentration value of the second gas delivered through the patient delivery conduit. In one embodiment, the control unit is configured to integrate a first flow measurement signal received from the first flow sensor, a second flow measurement signal received from the second flow sensor, and a third flow measurement signal received from the third flow sensor to calculate a concentration value of the second gas. In one embodiment, the control unit is configured to calculate a concentration value of the second gas delivered through the patient delivery conduit in real time with each breath of a patient. In one embodiment, the control unit is configured to trigger an alarm based on a calculation comparing two integrated flow values to a third integrated flow value. In one embodiment, the control unit is configured to trigger an alarm base on a calculation comparing two instantaneous flow values to a third instantaneous flow value. In one embodiment, the system includes an input device electrically coupled to the control unit, wherein the control unit is configured to receive input from the input device including both a target patient gas concentration and a source gas concentration. In one embodiment, the system includes a pressure monitoring element disposed on the second branch conduit and electrically coupled to the control unit. In one embodiment, the pressure monitoring element is a pressure transducer. In one embodiment, the first gas source is a unit dose container comprising the first gas, and wherein the control unit is configured to receive a pressure measurement signal from the pressure monitoring element and activate a safety feature corresponding to the received pressure measurement signal. In one embodiment, the control unit is configured to activate a safety feature based on a comparison of a value corresponding to a change in the received pressure measurement signal and an integral of a flow measurement signal received from at least one of the first, second and third flow sensors. In one embodiment, the control unit is configured to activate a safety feature that automatically shuts off the flow of gas when a threshold integral measurement is reached.

In one embodiment, a method for monitoring an inspired gas concentration in a system includes a first branch conduit and a second branch conduit, where the first branch conduit is fluidly connected to a first gas source and the second branch conduit is fluidly connected to a second gas source and a valve, and where the first and second branch conduits merge into a patient delivery conduit. The method includes the steps of receiving a first flow measurement received from the first branch conduit upstream of the merger, receiving a second flow measurement received from the second branch conduit downstream of the valve, and adjusting the valve corresponding to the received first and second flow measurements and a preset target concentration. In one embodiment, the method includes the steps of integrating the first flow measurement, integrating the second flow measurement, and adjusting the valve corresponding to the integrated first and second flow measurements. In one embodiment, the method includes the step of sending a correction signal to the valve based on the first flow measurement. In one embodiment, the method includes the step of sending a correction signal to the valve based on an integration of the first flow measurement. In one embodiment, the method includes the step of calculating a concentration value of the second delivered through the patient delivery conduit gas based on the first and second flow measurements. In one embodiment, the method includes the step of calculating a concentration value of the second gas delivered through the patient delivery conduit based on an integration of the first and second flow measurements. In one embodiment, the method includes the step of triggering an alarm based on a calculation comparing two flow values to a third flow value. In one embodiment, the method includes the step of triggering an alarm based on a calculation comparing two integrated flow values to a third integrated flow value. In one embodiment, the method includes the step of activating a safety feature based on a pressure measured from the second branch conduit. In one embodiment, the method includes the step of activating a safety feature based on both a change in the pressure measured from the second branch conduit and an integrated first flow measurement.

In one embodiment, a method for monitoring an inspired gas concentration in a branched breathing including a first branch conduit and a second branch conduit, where the first branch conduit is fluidly connected to a first gas source and the second branch conduit is fluidly connected to a second gas source, and where the first and second branch conduits merge into a patient delivery conduit, includes the steps of measuring the flow of gas in the first branch conduit, measuring the flow of gas in the second branch conduit, measuring the flow of gas in the patient delivery conduit, comparing the total flow of gas in or to the patient delivery conduit to at least one of the measured flow of gas in the first and second branch conduits, and determining the blend of gas in the patient delivery conduit. In one embodiment, the method includes the step of comparing the measured flow of gas further comprises comparing the flow of gas in the first or second branch conduit to the total flow of gas in the patient delivery conduit. In one embodiment, the method includes the step of comparing the measured flow of gas further comprises comparing the flow of gas in the first or second branch conduit to the sum total flow of measured gas in both the first and second branch conduits. In one embodiment, the method includes the step of comparing first the flow of gas in the first or second branch conduit to the total flow of gas in the patient delivery conduit, comparing second the flow of gas in the first or second branch conduit to the sum total flow of measured gas in both the first and second branch conduits, and determining if the first and second comparisons are equal. In one embodiment, the method includes the step of triggering a safety feature or an alarm based on if the first and second comparisons are not equal. In one embodiment, the method includes the step of adjusting the flow of gas from at least one of the first and second gas sources based on the determined blend of gas in the patient delivery conduit. In one embodiment, the method includes the step of triggering an alarm based on the determined blend of gas in the patient delivery conduit. In one embodiment, the method includes the step of triggering a safety feature or an alarm based on a pressure measured from the second branch conduit. In one embodiment, the method includes the step of activating a safety feature based on both a change in a pressure measured from the second branch conduit and an integrated first flow measurement.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 5 is a flow chart of steps for measuring the flow of gas, calculating the concentration of blended gas, and determining whether to continue monitoring or trigger an alarm according to one embodiment.

DETAILED DESCRIPTION OF THE INVENTION

Figure 1:
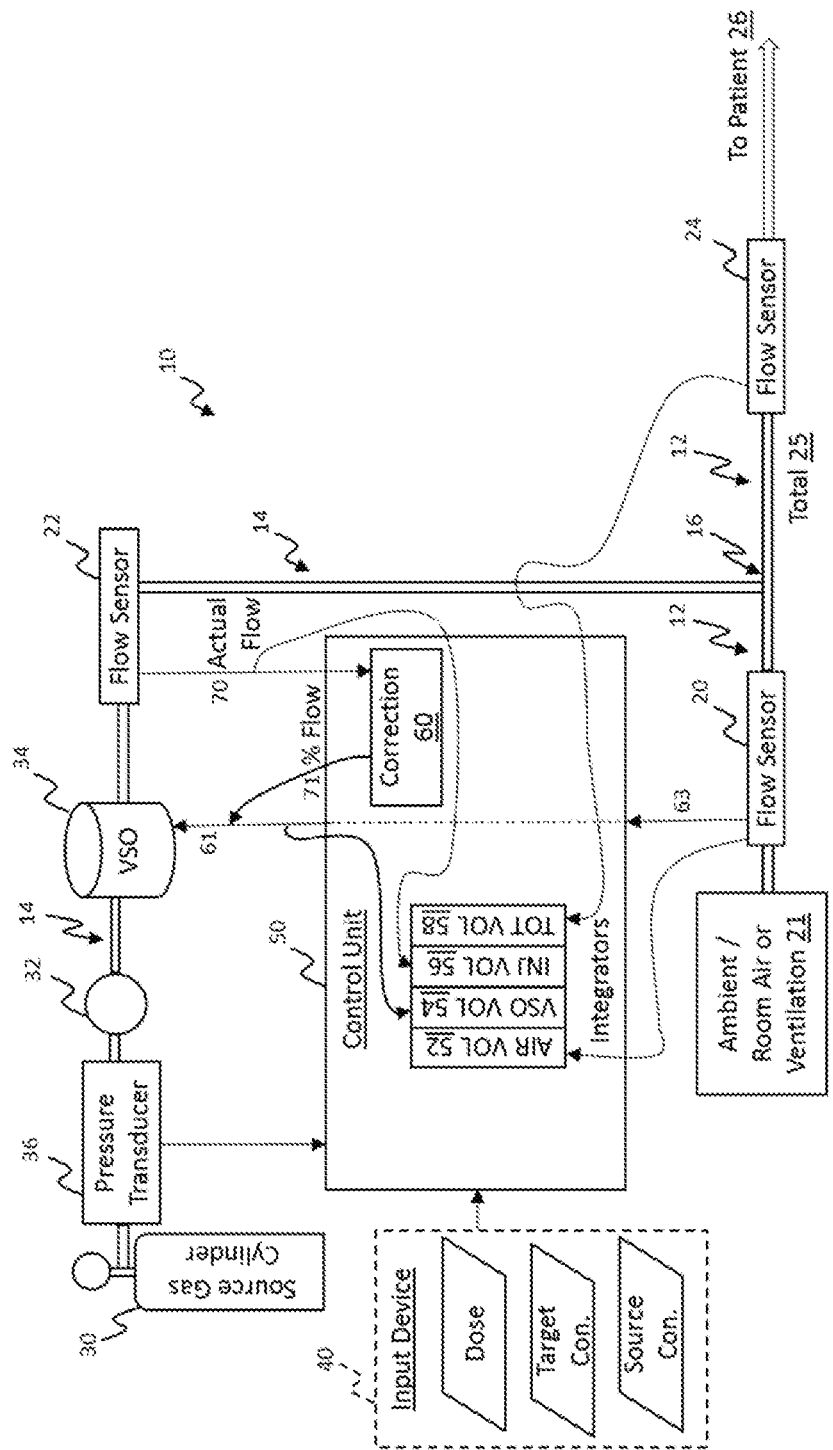
FIG. 1 is diagram of a system used to monitor inspired gas concentrations according to one embodiment.

It is to be understood that the figures and descriptions of the present invention have been simplified to illustrate elements that are relevant for a more clear comprehension of the present invention, while eliminating, for the purpose of clarity, many other elements found in systems and methods of monitoring inspired gas concentrations without the use of a complex or conventional gas analyzer. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein.

The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

"VSO" as used herein means voltage sensitive orifice. By way of example, "VSO" means any electrically controlled proportional flow control valve.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is system and method for monitoring inspired gas concentrations without the use of a complex or conventional gas analyzer.

In one embodiment, as shown in FIG. 1, system 10 may include first, second and third airway flow sensors 20, 22 and 24 positioned to detect flow rates of gases and air through first and second airways 12, 14. In the exemplary embodiment, the first airway 12 is a conduit that connects the patient outlet 26 to the second airway 14 and a low pressure gas or air source 21, which in certain embodiments is room or ambient air, a ventilator, or a container holding low pressure air. A first flow sensor 20 is upstream of where the first airway 12 merges 16 with the second airway 14, and downstream of the low pressure air source 21. The second airway 14 is a conduit that connects the source gas cylinder 30 to a pressure regulator 32 and a voltage sensitive orifice (VSO) 34, merging 16 with the first airway 12 downstream of the VSO. A second flow sensor 22 is positioned in the second airway 14 downstream of the VSO 34 and upstream of the merger 16 of the first airway 12 and second airway 14. A third flow sensor 24 is positioned in the first airway 12, downstream of the merger 16 of the first and second airways 12, 14. The airway flow sensors can be flow sensors known in the art, which may be for example a vane meter sensor or a hot wire sensor. A source gas cylinder 30 holds a source gas, which in one embodiment is in line with a pressure regulator 32 for regulating the pressure of the source gas entering the system 10. In one embodiment the pressure regulator brings the pressure in the second airway 14 down to 10-100 psi. In one embodiment, the pressure regulator brings the pressure down to 30 psi. As mentioned above, a first airway flow sensor 20 is positioned in the first airway 12 that delivers the low pressure air or dilution gas to the patient, which could come from a ventilator, room air or any other breathable gas source 21 and can be either driven by a device or drawn through the first airway flow sensor 20 by the patient. In certain embodiments, the pressure differential of the low pressure gas source 21 is 0-5 psi. In certain embodiments, the pressure differential of the low pressure gas source 21 is less than 4 psi. In certain embodiments, the pressure differential of the low pressure gas source 21 is less than 3 psi. In certain embodiments, the pressure differential of the low pressure gas source 21 is less than 2 psi. In certain embodiments, the pressure differential of the low pressure gas source 21 is less than 1 psi. In certain embodiments, the low pressure gas source 21 is an unpressurized source, such as ambient room air.

In one embodiment, the gas concentration of the source gas cylinder 30 and a target gas concentration for inhalation by the patient 26 is entered via an input device 40 into a control unit 50. The target gas concentration can be determined by a medical professional, based on the type of treatment being administered, and the characteristics of the patient being treated. The first flow sensor 20 sends a signal 63 to a control unit 50 of a flow measurement of the flow of air driven by a device or drawn by the patient from the low pressure air source 21. This signal 63 is processed by the control unit 50. Based on knowing the concentration of gas in the source gas cylinder 30, and the amount of air pulled into the first airway 12 from the low pressure gas source, the control unit can calculate an appropriate amount if gas to allow through the VSO 34 to match the total 25 diluted target gas concentration for inhalation by the patient 26. The control unit then sends the appropriate valve drive signal 61 to the input of the VSO 34. The control unit 50, which in certain embodiments is a microcontroller, can process flow information in terms of instantaneous flow, or a calculated volume based on an integrated measurement of flow over time, as explained in further details below.

In one embodiment, the second airway flow sensor 22 sends an instantaneous actual airflow signal 70 to a correction module 60 of the control unit 50, which in one embodiment is driven by a microprocessor. Control unit 50 may further include any other hardware, software, memory and circuitry suitable for storing and running system 10 applications (such as modules 52, 54, 56 and 58), and for communicating with other local or remote computing devices. Signal 70 may be indicative of the actual flow measured from the output of an electronically controlled airflow valve, which in one embodiment is a VSO/proportional control valve 34. In one embodiment, the second airway flow sensor 22 is a high precision injector flow sensor that measures the actual flow coming out of the VSO 34. The second airway flow sensor 22 sends a signal 70 to the control unit 50 of the actual flow and allows the control unit 50 to send an output correction signal 71 to the VSO 34 valve drive signal 61 to fine tune the actual flow to the absolute desired flow. For example, after receiving the actual airflow signal 70, the control unit 50, under digital control, sends a correction signal 71 to the VSO 34 valve drive signal 61 to release a flow proportional to the actual airflow detected by the first airway flow sensor 20. In one embodiment, the correction signal 71 is used to calculate the ratio of the flow that matches the set concentration percentage. In one embodiment, the voltage of the correction signal is proportional to the flow it wants the VSO 34 to deliver, and there is a reasonably close relationship between the voltage and the flow output. Inputs into the system include dosages, target concentrations desired for the patient 26, and source concentrations for source gases 30. An input device 40 such as a smart phone, tablet, laptop or any other computing device can be used to communicate with the control unit 50 via any communications network understood in the art, including wireless systems like radio frequency identification (RFID) systems, BLUETOOTH systems, near-filed communication systems, etc.

This closed loop system microcontroller control unit, along with a pair of serially placed flow sensors 20, 24 in the first airway 12 to measure subject inspired flow and total inspired flow (including injected flow) enables both the instantaneous and breath-by-breath detection of errors in gas concentration delivery. The system according to embodiments described herein replaces the conventional gas analyzer that is normally positioned where the third flow sensor 24 is, for analyzing the total diluted output gas mixture flowing to a patient. By knowing the concentration of the source gas cylinder 30, the system according to the embodiments can calculate and regulate the total diluted output gas mixture. Embodiments can provide and display a calculation of the actual concentration delivered, and can activate an alarm when the actual concentration delivered is outside the preset alarm limits. The control unit, by knowing the target gas concentration desired to be delivered and the concentration of the source gas, can determine the correct percentage of the flow to the patient that should be released by the VSO 34 and can detect if any component of the gas mixing system malfunctions.

To assure that the gas blend being delivered to the patient is correct, the total blended gas concentration may be calculated, without requiring the use of a gas analyzer. In one embodiment, an additional third airway flow sensor 24 that measures the total flow 25 from the system 10 to the patient is utilized. Volume calculations can also be utilized in the system, and in one embodiment, integration modules are utilized in the control unit 50 for converting flow measurements to volume measurements. For example, in one embodiment, instantaneous flow measurements are used to calculate a total gas concentration. For example, in one embodiment, the second flow sensor 22 measurement is divided by the third flow sensor measurement 24 and the input source gas concentration is then factored in for determining a total gas concentration 25 going to the patient 26. Proper operation of the system 10 can be confirmed by checking to make sure that the total flow measurement from the third sensor 24 matches the sum of the flow measurements of the first and second flow sensors 20, 22. In another embodiment, gas concentration is calculated based on integrated flow, or volume. For example, the control unit 50 can integrate the flow measured by the first airway flow sensor 20 that occurs during a single breath, and can calculate the volume of the breath utilizing an air volume integrator module 52. The flow detected by the second airway flow sensor 22 can also be integrated by an injection volume integrator module 56. With these two volume values, the control unit 50 can add the volume of the single breath to the injected volume of the source gas for concentration calculations. In one embodiment, as part of an analyzer function, the control unit 50 can divide the injected volume by the volume detected by the third airway flow sensor 24 (calculated by a total volume integrator module 58), and that proportion times the concentration in the source gas cylinder is the mean source gas concentration during that breath. Corrected VSO volume as calculated by a VSO volume integrator module 54 can also be compared to the injected flow volume calculated by the injection volume integrator module 56 for modifying the correction signal 71. Any display or interface depicting the mean source gas concentration value may be used as would be understood by those skilled in the art. In certain embodiments, mean source gas concentration values are calculated by the control unit in real time with each breath. In one embodiment, a flow based analyzer and alarm system are incorporated into or connected to the control unit 50, and perform multiple comparisons of integrated flow for each breath. In one embodiment, the control unit 50 drives the VSO 34 with a digital value proportional to the flow it wants to release. The control unit 50 can integrate the flow signal value by utilizing a VSO flow integrator module to approximate the volume of gas injected during the breath. The control unit can also integrate the flow signal 70 from the high precision injector flow sensor 22 in an injection flow integrator module to calculate the actual volume of gas ejected from the VSO. Embodiments of the system 10 therefore provide at least two values for quantifying the injected volume of gas.

In one embodiment, for alarm and monitoring functions, the system 10 can compare several integrated volumes. For example, in one embodiment, a comparison of the two injector volumes (integrated VSO drive signal vs. injector volume) can trigger an alarm if there are significant differences between the expected and actual values. In another example, a comparison between the first airway flow volume detected at sensor 20 and the third airway flow volume detected at sensor 24 less the actual flow injected volume would trigger an alarm that one of these two flow sensors requires service. If the calculated concentration, as based on the injected volume and total volume are outside the alarm limits, an alarm can be activated. It will be apparent to those having ordinary skill in the art that different combinations of measurements from at least two of the first, second and third airway flow sensors can provide calculated concentration values of the source gas going to the patient without using a gas analyzer. Thus, the integrators provide cross checks on all three flow sensors and the VSO so that a failure in any one of these can be detected by flow or integrated flow (i.e. volume) values from the other three. In one embodiment, the alarm is at least one of a visual and an audio alarm. In the event of an alarm, the control unit 50 can be configured to turn off gas valves and shut down the system based on the type of alarm and whether or not a preset difference threshold is measured.

Figure 2:
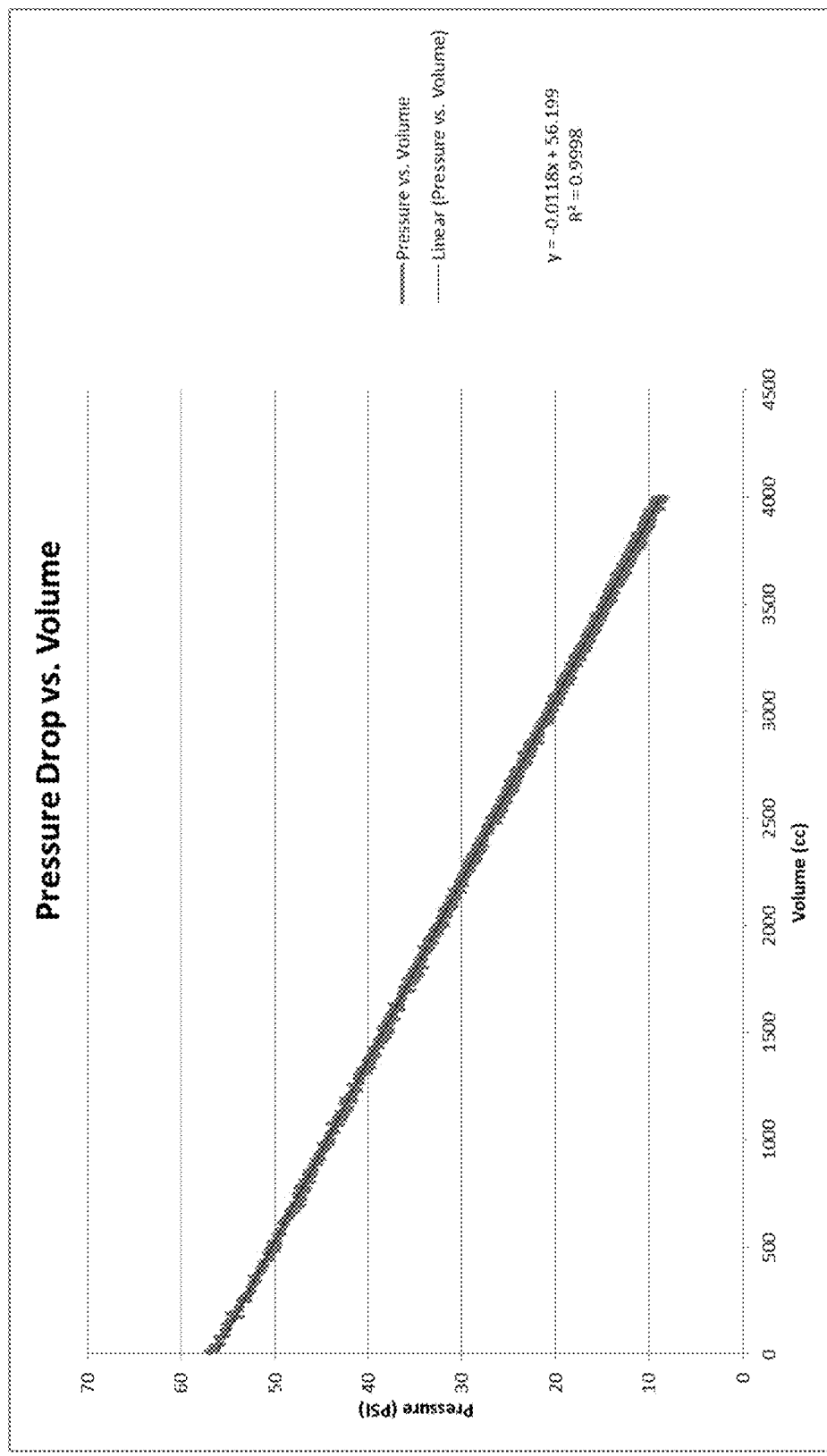
FIG. 2 is a graph of pressure drop vs. volume of gas consumed according to one embodiment.
Figure 3:
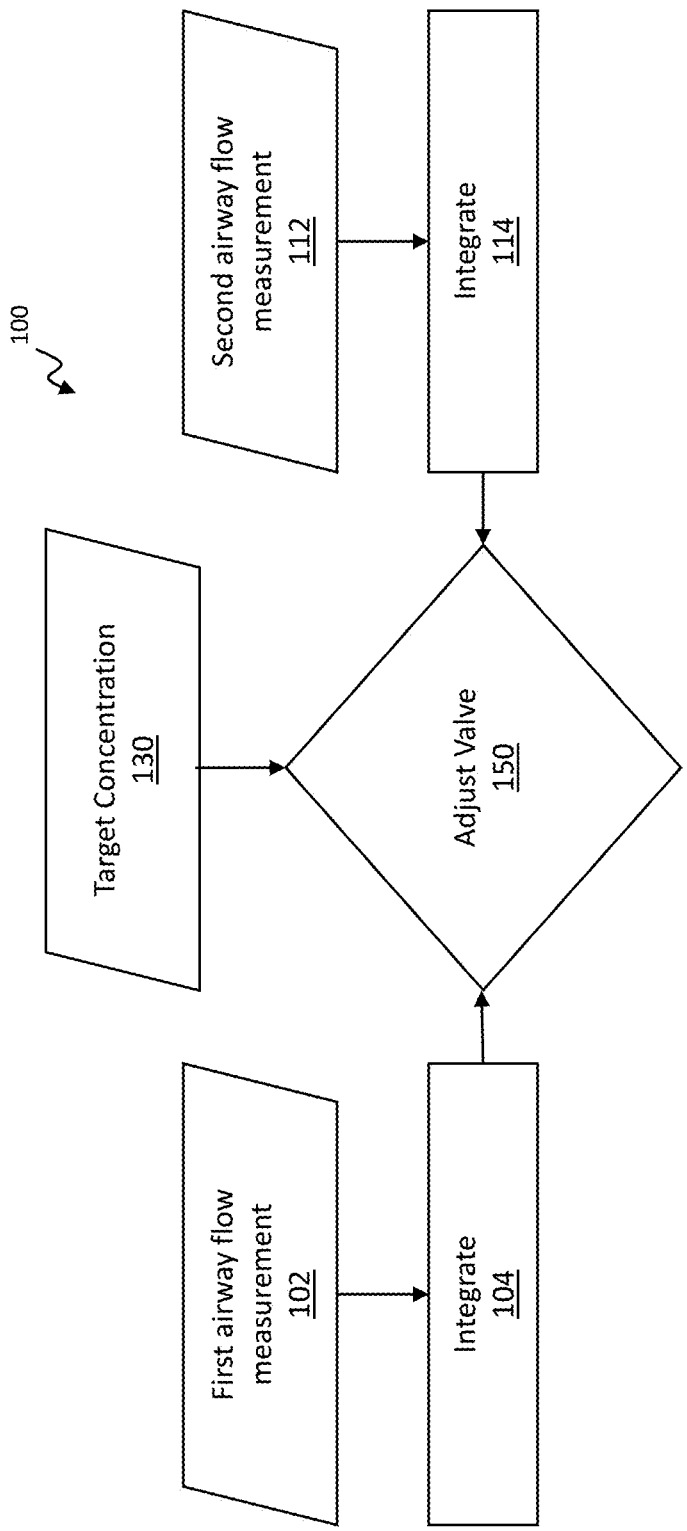
FIG. 3 is a flow chart of a method for monitoring an inspired gas concentration in a system according to one embodiment.

In one embodiment, as an additional backup monitoring function, the pressure in the source gas cylinder is monitored by a pressure monitoring element such as a pressure transducer 36 that is electrically coupled to the control unit 50. Most therapeutic gas systems use a large cylinder for convenience. However, when using a large cylinder, only a small percentage is used per breath or per minute. Therefore the changes in cylinder pressure are too small to detect a meaningful variance in rate of gas usage. However, when using a unit dose gas cylinder (meaning all of the gas in the cylinder is used during the treatment), the fall in pressure based of the volume of gas consumed per minute is relatively linear and predictable as shown in FIG. 2, and therefore can be used as an alarm to indicate an error in concentration delivery. In one embodiment, the control unit 50 calculates the volume consumed during a set time increment. In one embodiment, the control unit 50 calculates the volume consumed each 10-15 seconds and compares it to: (1) the volume calculated by the integral of the injector flow sensor during that period, and (2) the expected consumption based on the volume integral of the first airway flow sensor and the set inspired concentration to the pressure change in the source gas cylinder during that period. If either of these falls outside a set limit, an alarm would sound.

In one embodiment, a system is monitored by a method 100 for monitoring an inspired gas concentration. The system can include a first airway that includes a connection between a first gas source and a valve, and a second airway connecting a second gas source and the first airway to a patient outlet. In one embodiment, the method 100 includes the steps of integrating 104 a first airway flow measurement from the second airway 102, integrating 114 a second airway flow measurement from the second airway 112, and adjusting the valve 150 corresponding to the integrated first and second airway flow measurements 104, 114 and a preset target concentration 130. In one embodiment, a correction signal can be sent to the valve based on an integrated flow measurement from the second airway. In one embodiment, a concentration valve of the first gas is calculated based on the integrated first and second airway flow measurements.

In one embodiment, a method for monitoring an inspired gas concentration in a system is provided. The system includes a first branch conduit and a second branch conduit, where the first branch conduit is fluidly connected to a first gas source and the second branch conduit is fluidly connected to a second gas source and a valve. The first and second branch conduits are fluidly connected to a patient delivery conduit. The method includes integrating a first flow measurement received from the first branch conduit, and integrating a second flow measurement received from the second branch conduit downstream of the valve. The valve is adjusted corresponding to the integrated first and second flow measurements and a preset target concentration. In one embodiment, a correction signal is sent to the valve based on the integrated first flow measurement. In one embodiment, a concentration value of the first gas is calculated based on the integrated first and second flow measurements. In one embodiment, an alarm is triggered if a comparison of the integrated first and second airway flow measurements exceeds a threshold value. In one embodiment, a safety feature is activated based on a pressure measured from the second branch conduit. In one embodiment, the safety feature is activated based on both the pressure measured from the second branch conduit and the integrated first flow measurement.

Figure 4:
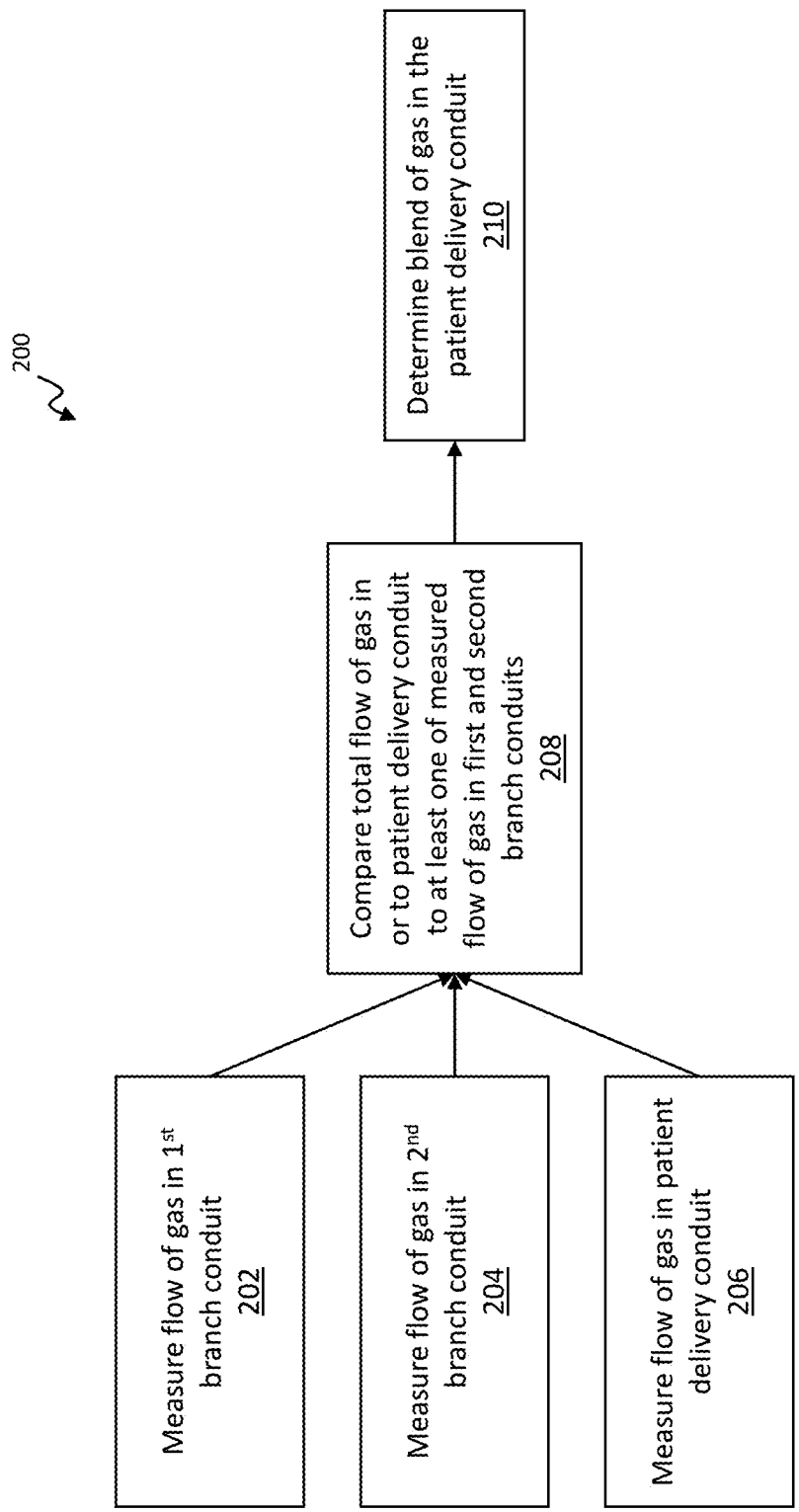
FIG. 4 is a flow chart of another method for monitoring an inspired gas concentration in a system according to one embodiment.

In another embodiment a method 200 for monitoring an inspired gas concentration in a branched breathing circuit is disclosed with reference now to FIG. 4. As similarly depicted in the circuit of FIG. 1, the circuit includes a first branch conduit and a second branch conduit. The first branch conduit is fluidly connected to a first gas source and the second branch conduit is fluidly connected to a second gas source. The first and second branch conduits merge into a patient delivery conduit. The flow of gas is measured in the first branch conduit 202, the flow of gas is measured in the second branch conduit 204, and the flow of gas is measured in the patient delivery conduit 206. The total flow of gas in or to the patient delivery conduit is compared to at least one of the measured flow of gas in the first and second branch conduits 208. The blend of gas in the patient delivery conduit is then determined 210, for example, as a percentage of flow of known concentrations from the first and/or second gas sources. Shown in more detail in FIG. 5, according to one embodiment, a first comparison of the flow of gas in the first or second branch conduit is compared to the total flow of gas in the patient delivery conduit 208A, generating a first determined value relating to the concentration of blended gas. Alternatively, or in parallel, a second comparison of the flow of gas in the first or second branch conduit is compared to the sum total flow of measured gas in both the first and second branch conduits 208B, generating a second determined value relating to the concentration of blended gas. While either of the first or second comparisons can be used to arrive at a determined concentration of blended gas (assuming known starting concentrations of individual gas sources), in another embodiment, the first and second comparison values can then themselves be compared to see if they are equal 209. If they are equal, the system continues monitoring. If they are not equal, an alarm or safety feature is triggered, as this would be indicative that one or more of the sensors in the system is malfunctioning. In one embodiment, comparing the measured flow of gas includes the step of comparing the flow of gas in the first or second branch conduit to the total flow of gas in the patient delivery conduit. In one embodiment, comparing the measured flow of gas further includes the step of comparing the flow of gas in the first or second branch conduit to the sum total flow of measured gas in both the first and second branch conduits. In one embodiment, comparing the measured flow of gas includes the step of comparing first the flow of gas in the first or second branch conduit to the total flow of gas in the patient delivery conduit, comparing second the flow of gas in the first or second branch conduit to the sum total flow of measured gas in both the first and second branch conduits, and determining if the first and second comparisons are equal. Accordingly, it should be appreciated that when the first and second comparisons are equal, the function of each sensor measuring flow is working properly. However, if the first and second comparisons are not equal, then at least one of the sensors in the breathing circuit is malfunctioning, and appropriate action can be taken. In one embodiment, a safety feature or an alarm is triggered based on if the first and second comparisons are equal. In one embodiment, the method includes the step of adjusting the flow of gas from at least one of the first and second gas sources based on the determined blend of gas in the patient delivery conduit. An alarm can be triggered based on the determined blend of gas in the patient delivery conduit. A safety feature or an alarm can also be triggered based on a pressure measured from the second branch conduit. In addition, a safety feature can be triggered based on both a change in a pressure measured from the second branch conduit and an integrated first flow measurement.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A system for monitoring an inspirable gas concentration for delivery to a patient, comprising:
   a pumpless branched breathing circuit comprising a first branch conduit and a second branch conduit, wherein the first branch conduit is fluidly connected to a first gas source having a first gas concentration and the second branch conduit is fluidly connected to a second gas source having a second gas concentration, wherein the first and second branch conduits merge directly into a patient delivery conduit without passing through a mixing chamber or a mixed gas control valve, wherein the patient delivery conduit downstream of the merge does not comprise a pressure sensor, and wherein the pumpless branched breathing circuit does not comprise an exhalation valve;

a first flow sensor in the first branch conduit configured to generate a first flow measurement, a second flow sensor in the second branch conduit configured to generate a second flow measurement, and a third flow sensor in the patient delivery conduit configured to generate a third flow measurement; and a control unit electrically coupled to the first, second and third flow sensors;

wherein the control unit is configured to:
  determine a blended gas concentration comprising the second gas in a blend of gas in the patient delivery circuit based on the third flow measurement and at least one of the first and second flow measurements, and
  monitor in parallel, first and second comparisons, triggering an alarm or a safety feature when the first or second comparisons fail, the first comparison based on comparing a sum of the first and second flow measurement to the third flow measurement, and the second comparison based on comparing the blended gas concentration in the patient delivery conduit to a preset target patient gas concentration.

2. The system of claim 1, wherein the second gas source is a pressurized container comprising the second gas.

3. The system of claim 1, wherein the first gas source is at least one of a ventilator, room air and ambient air.

4. The system of claim 1, wherein the first gas source is pressurized to a pressure differential of less than 3 psi.

5. The system of claim 1, wherein the first gas source is unpressurized air.

6. The system of claim 1 further comprising:
a valve in the second branch conduit upstream of the second flow sensor;
wherein the control unit is configured to adjust the valve based on the first, second and third flow measurements.

7. The system of claim 6, wherein the valve is a proportional flow control valve.

8. The system of claim 1, wherein the control unit is a microcontroller.

9. The system of claim 1, wherein the control unit is configured to generate a correction signal based on a flow measurement signal received from the second flow sensor.

10. The system of claim 9, wherein the control unit is configured to integrate one or more of the first, second and third flow measurements.

11. The system of claim 1, wherein the control unit is configured to accept a source gas concentration value and a target patient gas concentration value as input.

12. The system of claim 1, wherein the control unit is configured to calculate a concentration value of the second gas delivered through the patient delivery conduit in real time with each breath of a patient.

13. The system of claim 1, wherein the control unit is configured to trigger the alarm based on a calculation comparing two integrated flow values of the measured flow from at least one of the first and second flow sensors to a third integrated flow value of the measured flow from at least one of the first and second flow sensors.

14. The system of claim 1, wherein the control unit is configured to trigger the alarm based on a calculation comparing two instantaneous flow values to a third instantaneous flow value.

15. The system of claim 1 further comprising:
an input device electrically coupled to the control unit, wherein the control unit is configured to receive input from the input device including both the target patient gas concentration and at least one of the first and second gas concentrations.

16. The system of claim 1 further comprising:
a pressure monitoring element disposed on the second branch conduit and electrically coupled to the control unit.

17. The system of claim 16, wherein the pressure monitoring element is a pressure transducer.

18. The system of claim 16, wherein the first gas source is a unit dose container comprising the first gas, and wherein the control unit is configured to receive a pressure measurement signal from the pressure monitoring element and activate the safety feature corresponding to the received pressure measurement signal.

19. The system of claim 18, wherein the control unit is configured to activate the safety feature based on a value corresponding to a change in the received pressure measurement signal and an integral of a flow measurement signal received from at least one of the first, second and third flow sensors.

20. The system of claim 1, wherein the control unit is configured to activate the safety feature that automatically shuts off the flow of gas from at least one of the first or second gas source when a threshold integral measurement of measured flow from at least one of the first and second flow sensors is reached.

21. A method for monitoring an inspired gas concentration in a branched breathing circuit, the method comprising:
providing a pumpless branched breathing circuit comprising a controller, a first branch conduit and a second branch conduit, wherein the first branch conduit is fluidly connected to a first gas source having a first gas concentration and the second branch conduit is fluidly connected to a second gas source having a second gas concentration, wherein the first and second branch conduits merge directly into a patient delivery conduit without passing through a mixing chamber or a mixed gas control valve, wherein the patient delivery conduit downstream of the merge does not comprise a pressure sensor, and wherein the pumpless branched breathing circuit does not comprise an exhalation valve, the controller executing a method comprising the steps of;
measuring a flow of gas in the first branch conduit;
measuring a flow of gas in the second branch conduit;
measuring a flow of gas in the patient delivery conduit;
comparing the measured flow of gas in the patient delivery conduit to at least one of the measured flow of gas in the first and second branch conduits;
determining a blended concentration comprising the second gas in a blend of gas in the patient delivery conduit; and
monitoring in parallel, first and second comparisons, triggering a safety feature or an alarm if the first or second comparisons fail, the first comparison based on comparing a sum of the measured flow of gas in the first branch conduit first and the measured flow of gas in the second branch conduit to the measured flow of gas in the patient delivery conduit, and the second comparison based on comparing the blended concentration in the patient delivery conduit to a preset target concentration.

22. The method of claim 21, wherein comparing the measured flow of gas further comprises comparing the measured flow of gas in the first or second branch conduit to the measured flow of gas in the patient delivery conduit.

23. The method of claim 21, wherein comparing the measured flow of gas further comprises comparing the measured flow of gas in the first or second branch conduit to the measured flow of measured gas in both the first and second branch conduits.

24. The method of claim 21, further comprising the step of adjusting the flow of gas from at least one of the first and second gas sources based on the determined blend of gas in the patient delivery conduit.

25. The method of claim 21, further comprising the step of triggering the alarm based on the determined blend of gas in the patient delivery conduit.

26. The method of claim 21, further comprising the step of triggering the safety feature or the alarm based on a pressure measured from the second branch conduit.

27. The method of claim 21, further comprising the step of activating the safety feature based on both a change in a pressure measured from the second branch conduit and an integrated first flow measurement.

\* \* \* \* \*